United States Patent [19]

Prestwich

[11] 4,455,441

[45] Jun. 19, 1984

[54] ATTRACTANT TERMITICIDAL COMPOUNDS, COMPOSITIONS AND METHODS OF USE THEREFOR

[75] Inventor: Glenn D. Prestwich, Stony Brook, N.Y.

[73] Assignee: Research Foundation of State University of New York, Albany, N.Y.

[21] Appl. No.: 423,006

[22] Filed: Sep. 24, 1982

[51] Int. Cl.$^3$ .................. C07C 33/42; C07C 31/34; A61K 31/045; A01N 31/02
[52] U.S. Cl. .................................. 568/843; 568/841; 568/842; 424/343; 424/350; 424/351; 424/DIG. 8; 424/DIG. 11
[58] Field of Search .............. 568/843, 842; 424/343, 424/351, DIG. 8, DIG. 11, 350

[56] References Cited

PUBLICATIONS

Gunstone, F. D., An Introduction to the Chemistry of Fats and Fatty Acids, New York, John Wiley, pp. 38-39, (1958).

Prestwich et al., "Flourolipids as Targeted Termiticides and Biochemical Probes", *Journal of Agric. and Food Chem.*, (1981), 29:1023-1027, Americal Chemical Society, Easton, Pa.

Mauldin et al., "Effect of Chlortetracycline and Other Antibiotics on Protozoan Numbers in the Eastern Subterranean Termite," *J. Econ. Entomol.*, 73:123-128, (1980).

*Primary Examiner*—Natalie Trousof
*Assistant Examiner*—Bruce D. Gray
*Attorney, Agent, or Firm*—Omri M. Behr

[57] ABSTRACT

Alpha - fluoro - omega - hydroxy straight chain hydrocarbons are utilized to form attractant termiticidal compositions which are safe and economical for the combatting of termites and related pests.

39 Claims, No Drawings

ATTRACTANT TERMITICIDAL COMPOUNDS, COMPOSITIONS AND METHODS OF USE THEREFOR

BACKGROUND OF THE INVENTION

Termites, and relates pests, constitute a significant economic threat in a modern society. While conventional insecticides, typically chlorinated hydrocarbons such as chlordane, DDT, aldrin, dieldrin and BHC can be effectively utilized to eradicate these pests, such insecticides pollute water, contaminate soil, and are toxic to many life forms. Chlordane is the only chlorinated hydrocarbon that has not yet been banned, principally because a suitable substitute having its effectiveness has yet to be found. However, it still accumulates in the environment and causes food chain elimination since, for instance, an earthworm may be resistant to its poison, but the bird which consumes many such earthworms may die or be rendered infertile. An environmentally inactive chemical is thus needed to obviate food chain problems. While the chlorinated hydrocarbon insecticides are economical to produce, the cost of the resulting environmental cleanup makes their use expensive in the long run. Thus, there exists a substantial need for new environmentally safe and effective pesticides.

For a pesticide to be effective against termites and related pests it must have a somewhat delayed onset of activity. Termites typically feast upon a food supply and then return to their nest and regurgitate the food to be shared by those occupying the nest. Thus, a pesticide which instantly destroys the feeding termites has absolutely no effect upon those hatching on the nest. While the feeding termites are affected, those in the nest continue to multiply and thus the infestation remains. A delayed onset of toxic effects would allow for the insects to return poisoned food to the entire colony and thereby poison all the occupants. Thus, in addition to high toxicity, an effective termite poison must have a delayed onset of activity and be easily transferable to other members of a given colony.

Furthermore, an effective pesticide must possess the more subtle characteristic of not only being a "non-repellent", but should most advantageously be an "attractant". This simply means that a feeding termite would not prefer another food source over the poisoned source and ideally would even prefer the poisoned source over a regular food supply.

Additional characteristics of an ideal pesticide would be nonleachability, i.e., poor solubility in water, and stability, i.e., not readily degraded in the soil.

DESCRIPTION OF THE INVENTION

The present invention relates to alpha-fluoro-omega-hydroxy straight chain hydrocarbons having a chain length of from 10 to 16 carbon atoms having from 0 to 5 double bonds therein and compositions containing same for the combatting of termites and related pests. While some of the alpha-fluoro-omega-hydroxy straight chain hydrocarbons utilizable in the present invention are known, the subgroup consisting of alpha-fluoro-omega-hydroxy straight chain alkenes having from 10 to 16 carbon atoms and having from 1 to 4 double bonds therein are heretofore unknown and therefore novel.

Preferred compounds of this invention are those having 1 or 2 double bonds and those having 12 or 14 carbon atoms. The double bonds are most preferably in the cis or Z geometry. Chain lengths of even numbers of carbon atoms i.e. 10,12,14 and 16 are also most preferred, with 12 being especially preferred.

Most especially preferred compounds are those of the formulae I and II.

wherein n is an integer of from 10 to 16; and

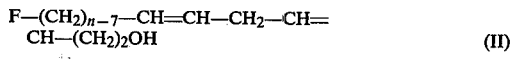

wherein n is an integer of from 10 to 16.

Of these compounds of formulae I and II, highly preferred are those wherein n is an even integer, i.e. 10,12,14 or 16, and/or those wherein the double bond or bonds are in the cis or Z position. Most highly preferred are those wherein n is 12. Representative compounds of this invention include:

10-fluoro-(Z)-3-decen-1-ol;
10-fluoro-(E)-3-decen-1-ol;
12-fluoro-(Z)-3-dodecen-1-ol;
12-fluoro-(E)-3-dodecen-1-ol;
14-fluoro-(Z)-3-tetradecen-1-ol;
14-fluoro-(E)-3-tetradecen-1-ol;
16-fluoro-(Z)-3-hexadecen-1-ol;
16-fluoro-(E)-3-hexadecen-1-ol;
10-fluoro-(Z),(Z)-3,6-decadien-1-ol;
12-fluoro-(Z),(Z)-3,6-dodecadien-1-ol;
14-fluoro-(Z),(Z)-3,6-tetradecadien-1-ol;
16-fluoro-(Z),(Z)-3,6-hexadecadien-1-ol;
12-fluoro-(Z),(E)-3,6-dodecadien-1-ol;
12-fluoro-(E),(E)-3,6-dodecadien-1-ol;
12-fluoro-(E),(Z)-3,6-dodecadien-1-ol;
10-fluoro-(Z),(Z)-3,5-decadien-1-ol;
12-fluoro-(Z),(Z)-3,5-dodecadien-1-ol;
14-fluoro-(Z),(Z)-3,5-tetradecadien-1-ol;
16-fluoro-(Z),(Z)-3,5-hexadecadien-1-ol;
12-fluoro-(Z),(E)-3,5-dodecadien-1-ol;
12-fluoro-(E),(E)-3,5-dodecadien-1-ol;
12-fluoro-(E),(Z)-3,5-dodecadien-1-ol; and
12-fluorododecan-1-ol.

Most surprisingly, the alpha-fluoro-omega-hydroxy straight chain hydrocarbons having chain lengths from 10 to 16 carbon atoms and 0 to 4 double bonds therein have been found to be attractant termiticidal agents. Thus, when a termiticidal amount of the alpha-fluoro-omega-hydroxy straight chain hydrocarbon is combined with a water-insoluble solid carrier ingestible by termites, a composition is formed which can be utilized to combat termites and related pests.

The compounds and compositions of the present invention possess the desirable attributes necessary for a safe, effective termiticide. The compounds resemble normal lipids which makes then non-repellent and/or attractive. This lipid-like character also makes them poorly soluble in water, so that they are substantially non-leachable, and stable, so that they are not readily degraded in the soil. They are nevertheless easily catabolized by beta-oxidation, which gives them the extremely desirable property of biodegradability.

While the preferred embodiments of this invention there are employed compounds having both attractant and termiticidal properties, the invention is not limited thereto.

The basic criterion is the active compound shall be termiticidal and have a toxicity differential vis a vis higher organism than termites. It is merely required that such compounds be non-repellant to termites since termites will normally seek out regular food sources such as cellulosic materials in particular wood which can be treated with such termiticidal compositions. The provision of bait blocks treated with such compositions, for example, but of course not limited to, 16-fluoro-Z/E 9-hexadecen-1-ol or 12-fluorododecan-1-ol are considered to be within the scope of the present invention.

It has been found advantageous to additionally provide such bait blocks comprising non-repellant termiticides with an attractant composition attracting the termites. Such attractant compositions may either comprise members of the groups disclosed herein which have termiticidal as well as attractant properties but can also include any compounds known to the art which have the property of being attractive to termites.

When tested in standardized test procedures for termiticidal activity, the compounds and compositions of the present invention exhibit high toxicity vis a vis *Reticulitermes flavipes*, the eastern subterranean termite. Thus, they are termiticidal (toxic) at levels of 1 to 100 mg/kg, or 4 to 400 ng/termite. A small amount of 10–500 mg is thus capable of destroying a typical 60,000 termite mature colony. Additionally, they have a delayed onset of activity, exhibiting the first toxic effects at 12–72 hours and 80% to 100% mortality at 48–180 hours.

The water-insoluble solid carrier ingestible by termites utilized in the compositions of the present invention are cellulose based preferably wood, i.e. most preferably a block of wood, which may also be partially enclosed by a water-insoluble sheath such as a plastic sheath to further reduce leaching but leaving enough surface to which the termites would typically be attached.

The termiticidal, attractant and termiticidal attractive compounds disclosed and discussed herein, and suitably the alpha-fluoro-omega-hydroxy straight chain hydrocarbon is applied to the carrier at a rate of about 0.05 to 1.0 percent (500 to 10,000 ppm). Preferably, they are applied to the carrier at a rate of about 0.5 to 1.0 percent (5000 to 10,000 ppm). Such application is very effective when carried out by vacuum treatment of the wood block with a solution of the active agent in a non-residual solvent, preferably acetone.

In addition to *Reticulitermes flavipes*, the compounds and compositions of the present invention are useful in combatting *Coptotermes formosanus* (Formosan termite) as well as other European, Asian, African, and South American pest termites. Typically, the alpha-fluoro-omega-hydroxy-straight chain hydrocarbon is applied to a suitable carrier, i.e. small blocks of wood, which are then provided to the termites as a food supply. The feeding termites ingest the treated carrier, travel back to the colony and regurgitate the treated carrier. The nest inhabitants ingest the treated carrier, and all are thereby affected, thus destroying the colony population.

Certain of the alpha-fluoro-omega-hydroxy-straight-chain alkenes of the present invention can be prepared by reaction of an appropriately protected alkyne of the formula III $$HC\equiv C-CH_2CH_2-OPr \qquad (III)$$

wherein Pr represents a readily removable alcohol protecting group, with n-butyl lithium to form the lithium salt followed by addition of the appropriate alpha-fluoro-omega-haloalkane of the formula IV $$X-(CH_2)_{n-4}-F \qquad (IV)$$

wherein n is 10–16 and X is bromo, iodo or chloro, preferably bromo to afford an intermediate of the formula V $$F-(CH_2)_{n-4}-CH\equiv CHCH_2CH_2OPr \qquad (V)$$

wherein n and Pr are as hereinbefore defined. Typical protecting groups are those such as benzyl tetrahydropyranyl and t-butyldimethylsilyl. This reaction is typically conducted in tetrahydrofuran containing a polar aprotic solvent such as hexamethyl phosphoric triamide. The formation of the lithium salt is most preferably conducted at low temperatures, i.e., −80° to about −50° C., and then the reaction mixture is allowed to warm to a higher temperature, i.e., about −10° to about 0° C. for the addition of the alpha-fluoro-omega-haloalkane of formula V.

The intermediate of formula V is then subjected to hydrogenation to afford an alkene of the formula VI.

$$F-(CH_2)_{n-4}-CH=CH-CH_2CH_2OPr \qquad (VI)$$

wherein n and Pr are as hereinbefore defined. Hydrogenation utilizing a palladium/barium sulfate/quinoline catalyst (or Lindler catalyst alternatively) affords predominately the cis (Z) compound, while the trans (E) compounds can be produced using sodium or lithium in liquid ammonia. Typically the hydrogenation is conducted at about room temperature utilizing a lower alkanol such as methanol as the solvent.

Removal of the protecting group (Pr) from the compounds of formula VI is typically effected by treatment with a weak acid or an acidic resin such as Dowex, and thus affords the desired compounds of formula I.

Compounds preparable by the immediately aforementioned process include:
10-fluoro-(Z)-3-decen-1-ol;
10-fluoro-(E)-3-decen-1-ol;
12-fluoro-(Z)-3-dodecen-1-ol;
12-fluoro-(E)-3-dodecen-1-ol;
14-fluoro-(Z)-3-tetradecen-1-ol;
14-fluoro-(E)-3-tetradecen-1-ol;
16-fluoro-(Z)-3-hexadecen-1-ol; and
16-fluoro-(E)-3-hexadecen-1-ol.

The compounds of this invention represented by formula II are conveniently prepared by treatment of 1-methoxy-1,4-cyclohexadiene with successively ozone and methanol, dimethyl sulfide and sodium borohydride to afford methyl 6-hydroxy-(Z)-3-hexenoate. The methyl 6-hydroxy-(Z)-3-hexanoate is then converted to a protected ether, suitably either a tetrahydroxypyranyl or triethylsilyl ether. This may be achieved by reaction with 3,4-dihydropyran and pyridinium p-toluenesulfonate in methylene chloride to give methyl 6-tetrahydropyranyloxy-(Z)-3-hexenoate, which is further treated with a reducing agent such as lithium aluminum hydride to afford 6-tetrahydropyranyloxy-(Z)-3-hexen-1-ol. The latter compound is converted to the corresponding terminal iodide or bromide, 1-iodo-6-tetrahydropyranyloxy-(Z)-3-hexene is formed by reaction with p-toluenesulfonyl chloride, followed by sodium iodide. Alternately, the 6-tetrahydropyranyloxy-(Z)-3-hexen-1-ol can be converted to the corresponding bromide.

Either the bromide or iodide is then reacted with triphenyl phosphine to form the 6-tetrahydropyranyloxy-(Z)-3-hexen-1-triphenylphosphonium iodide (or bromide). This iodide or bromide is then reacted with an omega hydroxy aldehyde of the formula VII

wherein n is as hereinbefore defined, to form the intermediate of the formula VIII

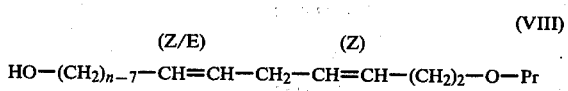

wherein n and Pr are as hereinbefore defined.

Treatment of the intermediate of formula VIII with diethylaminosulfur trifluoride in a halogenated hydrocarbon solvent at low temperatures (−80° to about −60° C.) affords the corresponding fluoro compund of formula IX

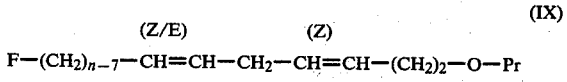

wherein n and Pr are as hereinbefore defined.

Removal of the Pr protecting group of the fluoro compound of formula IX utilizing a weak acid affords the desired compound of the formula X

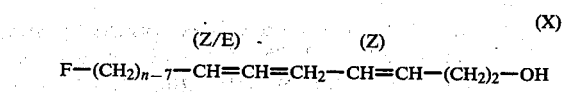

Compounds preparable by the immediately aforementioned route include:
10-fluoro-(Z),(Z)-3,6-decadien-1-ol;
10-fluoro-(Z),(E)-3,6-decadien-1-ol;
12-fluoro-(Z),(Z)-3,6-dodecadien-1-ol;
12-fluoro-(Z),(E)-3,6-dodecadien-1-ol;
14-fluoro-(Z),(Z)-3,6-tetradecadien-1-ol;
14-fluoro-(Z),(E)-3,6-tetradecadien-1-ol;
16-fluoro-(Z),(Z)-3,6hexadecadien-1-ol;
16-fluoro-(Z),(E)-3,6-hexadecadien-1-ol;

Certain 3,5-dienols of the formula X

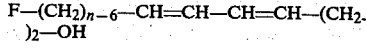

wherein n is as hereinbefore defined, are preparable by reaction of the lithium salt of the formula XI

wherein n is as hereinbefore defined, with the tetrahydropyranyl (or other suitable protecting group) ether of the formula XII

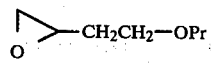

wherein Pr is as hereinbefore defined. This results in an intermediate of the formula XIII

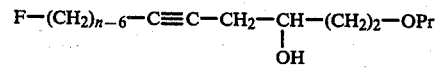

wherein n and Pr are as hereinbefore defined, which is then converted to the 3-halide, suitably the chloride and dehydrohalogenated in a conventional manner to afford a compound of the formula XIV

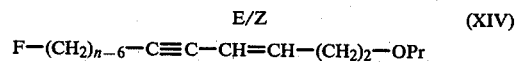

wherein n and Pr are as hereinbefore defined. Conversion to the chloride is typically accomplished using $PCl_5$. This dehydro halogenation is typically conducted utilizing an alkanolic base, suitably ethanolic potassium hydroxide. The 3E (trans) and 3Z (cis) isomers formed at this step can be separated by standard procedures known in the art, such as gas/liquid chromatography or high pressure liquid chromatography, although a mixture may be suitable for termiticidal formulations.

The compound of formula XIV is then hydrogenated in a known manner and then deetherified to produce the desired compounds of formula X. Hydrogenation utilizing hydrogen with a palladium/barium sulfate/quinoline catalyst produces primarily the cis (Z) compounds. The trans (E) compounds can be produced by utilizing sodium or lithium in liquid ammonia.

Compounds preparable by this immediately aforementioned method include:
10-fluoro-(Z),(Z)-3,5-decadien-1-ol;
12-fluoro-(Z),(Z)-3,5-dodecadien-1-ol;
14-fluoro-(Z),(Z)-3,5-tetradecadien-1-ol;
16-fluoro-(Z),(Z)-3,5-hexadecadien-1-ol;
10-fluoro-(Z),(E)-3,5-decadien-1-ol;
16-fluoro-(Z),(E)-3,5-hexadecadien-1-ol; and
12-fluoro-(Z),(E)-3,5-dodecadien-1-ol.

BIOASSAY OF FLUOROALKANOLS (PETRI DISH ASSAY)

Test compounds were dissolved in dry diethyl ether or dichloromethane and a 1.0 ml portion of the solution was pipetted onto a Gelman sterile 47-mm cellulose pad (Howard and Haverty, 1979). The ether was allowed to evaporate for 10 min, 1.0 ml of distilled water was added to the pad, and the pad was placed in a tight-sealing Gelman 50-mm plastic Petri dish.

Termites (*Reticulitermes flavipes* Kollar) were collected from rotten logs and tree stumps on the Stony Brook campus. Colonies were kept in trash cans in an insectary (85% RH, 27° C.) for a period of about 6 months before use in this experiment. The experiments were performed in an incubator at +28° C. Undifferentiated larvae above the third instar ("workers") were used in all toxicity tests. Termites were first shaken loose from the interior of the wood, then transferred using mouth aspirators and with soft forceps. The termites were held on filter paper for 24 hours, twenty healthy termites were added to each dish, and the number of dead which were then removed to prevent cannibalism was recorded at daily intervals.

| Structure | Activity of Fluoroalkanols | | Median Lethal-dose[c] mg/dish | Estimated[d] LD$_{50}$ (mice) (mg/kg) |
|---|---|---|---|---|
| | Maximum attractiveness (above 50% level) | Trail activity[a] | | |
| F(CH$_2$)$_6$C(H)=C(H)(CH$_2$)$_7$CH$_2$OH | NA | NA | 0.024 | 1.5(C$_{12}$satd.) 4.0(C$_{18}$satd.) |
| F(CH$_2$)$_{10}$C(H)=C(H)CH$_2$CH$_2$OH | NA | NA | 0.020 | 1.5(C$_{12}$satd.) 4.0(C$_{18}$satd.) |
| F(CH$_2$)$_8$C(H)=C(H)CH$_2$CH$_2$OH | 10$^{-7}$ 9 | 2 × 10$^{-8}$ 9 | .0093 | 1.5(C$_{12}$satd.) |
| F(CH$_2$)$_5$C(H)=C(H)CH$_2$—C(H)=C(H)CH$_2$CH$_2$OH | maximum 10$^{-7}$ 9 minimum 10$^{-8}$ 9 | <2 × 10$^{-10}$ | .012 | 1.5(C$_{12}$satd.) |
| F(CH$_2$)$_{11}$CH$_2$OH | NA | (6/20) | .0077 | 1.5 |
| F(CH$_2$)$_{10}$CH$_2$OH | NA | (6/20)[b] | .062 | >100(C$_{11}$satd.) |
| F(CH$_2$)$_6$C(H)=C(H)CH$_2$CH$_2$OH | NA | 6 × 10$^{-7}$ 9 | .0095 | 1.0(C$_{10}$satd.) |

Notes:
[a]Value is minimum quantity (in grams) per 10 cm required to elicit trail-following by a total of 8/20 termites in four trails.
[b]Maximum number of termites following at 5 × 10$^{-6}$ g/10 cm (highest conc. tested).
[c]Quantity of fluoro compound impregnated in filter pads required to cause 50% mortality at 3 days.
[d]Based on data from Pattison (1959) for the saturated omega-fluoro compounds. Information in parentheses gives estimates based on interpolation or indicates comparison compounds.

The following examples describe in detail compounds and compositions illustrative of the present invention and methods which have been devised for their preparation. It will be apparent to those skilled in the art that many modifications, both of materials and methods, may be practiced without departing from the purpose and intent of this disclosure.

Unless otherwise noted, materials are obtained from commercial suppliers and are used without further purification. Tetrahydrofuran (THF, Aldrich Gold Label) is distilled from sodium benzophenone in a circulating still, with a deep blue color being maintained in the distilling pot. Hexamethylphosphoric triamide (HMPA) is distilled from BaO and stored over molecular sieves (3 A°). Acetone is dried over potassium carbonate distilled and stored over molecular sieves (3 A°). Pyridine is dried over sodium hydroxide, distilled from BaO and stored over molecular sieves (3 A°). Hexane, ethyl acetate and methanol are Fisher HPLC grade and are used without further purification. p-Toluene-sulfonyl chloride is recrystallized from chloroform/petroleum ether (1:5 v/v). Toluene is dried by azeotropic distillation. Acetonitrile is distilled from calcium hydride. All reactions are performed under a nitrogen atmosphere.

H NMR spectra are recorded on a Varian HFT-80 (80 MHZ) spectrometer in deuterochloroform with tetramethylsilane as the internal standard. Data are reported in the form of δ values of signal (peak multiplicity, couping constant, if appropriate, number of protons). When peak multiplicities are reported, the following abbreviations are used: s, singlet; d, doublet; t, triplet; q, quartet; m, multiplet; br, broadened. $^{13}$C NMR spectra are recorded on a Varian CFT-20 (20 MHZ) spectrometer and proton noise decoupling and shifts are reported relative to tetramethylsilane (δ=0. ppm). Data are reported in the form of δ values of signal (peak multiplicity, and coupling constant if appropriate, intensity). Infrared spectra are obtained on a Perkin Elmer 727 instrument as a neat liquid. Data are given in cm$^{-1}$ with only the important diagnostic values reported.

Thin layer chromatography is performed by using MN Polygram Sil G/UV 254 (4×8) TLC plates. Visualization accomplished by UV light, iodine, or an ethanol-vanillin-H$_2$SO$_4$ reagent. Flash chromatography (Still et. al., J. Org. Chem., 43, 2923, 1978) is performed under N$_2$ pressure on Merck Silica Gel G (400-230 mesh) using hexane/ethyl acetate mixtures. Analytical gas-liquid chromatography (GC) is performed on a Varian model 3700 chromatograph (programmable temperature control) equipped with a flame ionization detector and nitrogen carrier gas.

EXAMPLE 1

A. 3-butyn-1-yl tetrahydropyranyl ether

A solution of 3-butyn-1-ol (3.0 g, 0.042 mol) and 3,4-dihydropyran (4.20 g, 0.05 mol) in hexane (10 ml) (Bongini et. al., Synthesis, 618, 1979), is added to a suspension of Dowex (1.5 g) in hexane (10 ml) and the mixture is stirred for 1 hr at room temperature. The resin is filtered off and the solvent removed in vacuo. The crude residue is purified by flash chromatography using hexane/ethyl acetate (9:1, v/v) to give 3-butyn-1-yl tetrahydropyranyl ether (6.47 g, 97%) as a colorless liquid: Rf=0.25; Hexane/ethyl acetate (1:1, v/v) IR (film) ν3300 (C≡C—H), 2160 (C≡C); and $^1$H NMR (CDCl$_3$) δ1.48 (m, 6H), 1.88 (t, J=3 Hz, 1H), 2.35 (m, 2H), 3.60 (m, 4H), 4.56 (br S, 1H).

EXAMPLE 2

8-bromo-1-fluoro-octane

A solution of 8-bromooctan-1-ol (Hendry et al., J. Chem. Ecol., 1, 317, 1975), (2.50 g, 11.9 mmol) in methylene chloride (about 3 ml) is slowly added to a stirred solution of diethylaminosulfur trifluoride (DAST) (Middleton, *J. Org. Chem,* 40, 574, 1975) (1.5 mL, 11.9 mmol) in methylene chloride (10 mL), cooled to −78° C. After the addition is completed, the reaction mixture is warmed to 25° C. and saturated aqueous sodium bicarbonate (about 5 mL) is added, followed by dilution with ether (about 200 mL). The organic layer is then separated, and washed with water (20 mL), saturated sodium bicarbonate (20 mL) and then dried (MgSO$_4$). The volatiles are removed in vacuo and the crude product is purified by flash chromatography using hexane/ethyl acetate, (95.5, v/v) to afford 8-bromo-fluorooctane (1.54 g, 61%) as a clear colorless liquid: Rf=0.70, hexane/ethyl acetate (7:3, v/v); IR (film) ν2850–3000 (alkane CH) and $^1$H-NMR (CDCl$_3$) δ1.15–2.0 (m, 12H), 3.39 (t, J=6 Hz, 2H), 4.42 (dt, J=48 Hz, 6 Hz, 2H).

EXAMPLE 3

12-fluoro-3-dodecyn-1-yl tetrahydropyranyl ether

To a solution of 3-butyn-1-yl tetrahydropyranyl ether (0.4815 g, 3.05 mmol) (prepared as in Example 1 above) in dry tetrahydrofuran (15 mL) at −78° C. is added n-butyllithium (3.05 mmol, 2.80 mL of 1.09M n-BuLi in hexane). The resulting yellow mixture is stirred for 1 hour at −78° C., warmed to −5° C. for about 5 min and then a solution of 8-bromo-1-fluorooctane (0.7716 g, 3.65 mmol, 1.2 eq.) in HMPA (10 mL) is added dropwise over 45 minutes (Hendry et al., *J. Chem. Ecol.,* 1, 317, 1975). After the addition is completed, the reaction is allowed to warm to room temperature and stirred overnight. After quenching the solution by the dropwise addition of water (about 10 mL), the aqueous solution is extracted with pentane (4×50 ml) and the combined pentane extracts are washed with saturated sodium chloride (50 mL) and dried (MgSO$_4$). The volatiles are removed in vacuo and the crude product is flash chromatographed using hexane/ethyl acetate (9:1, v/v) to give 12-fluoro-3-dodecyn-1-yl tetrahydropyranyl ether (0.526 g, 60%) as a clear colorless oil: Rf=0.60, hexane/ethyl acetate (7:3, v/v); IR (film) ν2850–3000 (alkane CH) and $^1$H-NMR (CDCl$_3$) δ1.20–1.90 (m, 18H), 2.05–2.20 (m, 2H), 2.30–2.55 (m,2H), 3.30–3.95(m, 4, 4.42 (dt, J=48 Hz, 6 Hz, 2H), 4.60 (br s, 1H).

EXAMPLE 4

12-fluoro-(Z)-3-dodecen-1-yl tetrahydropyranyl ether

A solution of 12-fluoro-3-dodecyn-1-yl tetrahydropyranyl ether (0.5262 g, 1.85 mmol) (prepared as in Example 3 above) in methanol (10 mL) containing about 4 drops of quinoline is hydrogenated at room temperature over 5% palladium on barium sulfate (25 mg). The mixture is kept at about 762 psi of hydrogen until 41.5 ml (1.85 mmol) of hydrogen has been absorbed. The catalyst is then filtered off and the solvent removed in vacuo. The residue is purified by flash chromatography using hexane/ethyl acetate (9:1, v/v) to give 12-fluoro-(Z)-3-dodecen-1-yl tetrahydropyranyl ether (0.52 g, 99%) as a clear oil: Rf=0.65, hexane/ethyl acetate (7:3, v/v); IR (film) ν3025 (C═CH); and $^1$H-NMR δ1.20–1.80 (m, 18H), 2.05 (m,2H), 2.35 (br q, J=4 Hz, 2H), 3.60 (m, 4H), 4.41(dt, J=48 Hz, 2H), 4.56 (br s, $^1$H), 5.41 (m, 2H).

EXAMPLE 5

12-fluoro-(E)-3-dodecen-1-ol

A solution of 12-fluoro-3-dodecyn-1-yl tetrahydropyranyl ether (1.42 g, 5 mmol) in dry tetrahydrofuran (50 ml.) is added slowly to a solution of sodium (920 mg., 40 mmol) in liquid ammonia (300 ml), the colour changing from blue through violet and red to a dull orange. More sodium (1.84 g, 80 mmol) is then added, the mixture becoming green then blue. The volume is increased to 500 ml. with liquid ammonia and the mixture stirred for two hours, after which dry ammonium chloride is added slowly until the color changed to pale yellow. After evaporation of the ammonia the residue is treated with dilute hydrochloric acid (6N., 50 ml.) and thoroughly extracted with ether. The neutral fraction is chromatographed on alumina (grade III, 30 g.). Elution with light petroleum yields 12-fluoro-(E)-3-dodecen-1-ol as a colourless oil, IR (film) 966 cm$^{-1}$ (Trans C═C).

EXAMPLE 6

12-Fluoro-(Z)-3-dodecen-1-ol

To a solution of 12-fluoro-(Z)-3-dodecen-1-yl tetrahydropyranyl ether (0.5242 g, 1.83 mmol) (prepared as in Example 5 above) in methanol (10 ml) is added Dowex resin (0.5 g) and the mixture is heated at 45° C. overnight (Bongini et. al., *Synthesis,* 618, 1979). The resin is then filtered off and the solvent is removed in vacuo. The crude product is purified by flash chromatography using hexane/ethyl acetate (93:7, v/v) to give 12-fluoro-(Z)-3-dodecen-1-ol (312 mg, 83%) as a clear colorless oil: Rf=0.36, hexane/ethyl acetate (7:3, v/v); IR (film ν3100–3550 (OH), 3000 (C═CH); and H NMR (CDCl$_3$) δ1.25–1.75 (m, 12H), 2.15 (m, 2H), 2.35 (br q, J=6 Hz, 2H), 3.65 (t, J=9 Hz, 2H), 4.41(dt, J=48 Hz, 6 Hz, 2H), 5.46 (m, 2H).

EXAMPLE 7

In accordance with the procedure of Examples 2–6 but utilizing 12-bromo-1-fluoro dodecane in place of starting with 8-bromo-1-fluorooctane there is obtained the corresponding hexadecen-1-ol.

Similarly where the bromo moiety of the starting material of Examples 2–7 is replaced by chloro or iodo, the same final products are obtained.

EXAMPLE 8

10-bromo-1-fluoro-decane

Repetition of the procedure described in Example 2 but using 1.00 g (4.23 mmol) of 10-bromodecanol and 0.5287 ml (4.23 mmol) of DAST in 50 mL methylene chloride affords the crude of 10-bromo-1-fluoro-decane. Purification by flash chromatography gives the 10-bromo-1-fluoro-decane (826 mg $^3$82%) as a clear colorless liquid: Rf=0.73 hexane/ethyl acetate (7:3, v/v); IR (film) δ2850–3000 (alkane CH); and $^1$H-NMR (CDCl$_3$) δ1.25–2.95 (m, 16H), 3.36 (t, J=6 Hz, 2H), 4.40 (dt, J=48 Hz, 2H).

EXAMPLE 9

14-fluoro-3-tetradecyn-1-yl tetrahydropyranyl ether

Repetition of the procedure described in Example 3 but using 1.106 g (7.0 mmol) of ether, 6.42 mL (7.0 mmol) of 1.09M n-butyl lithium in hexane, and 1.396 g (5.84 mmol, 1.2 eq) of 10-bromo-1-fluorodecane after purification by flash chromatography yields 14-fluoro-3-tetradecyn-1-yl tetrahydropyranyl ether (360 mg, 20%) as a clear yellowish oil: Rf=0.75 hexane/ethyl acetate (7:3, v/v); IR (film) ν2900 alkane CH); and $^1$H-NMR (CDCl$_3$) δ1.20–1.85 (m, 22H), 2.15 (m, 2H), 2.47 (m 2H), 3.65 (m 4H), 4.41 (dt, J=48 Hz, 6 Hz, 2H), 4.65 (br s, 1H).

EXAMPLE 10

14-fluoro-(Z)-3-tetradecen-1-yl-tetrahydropyranyl ether

Substantial repetition of the hydrogenation procedure described in Example 4 using 361.2 mg (1.16 mmol) of 14-fluoro-3-tetradecyn-1-yl tetrahydropyranyl ether and using 15 mg of 5% palladium on barium sulfate about 2 drops of quinoline in 10 mL of methanol with the reaction being stopped after 25.9 mL (1.16 mmol) of hydrogen has been absorbed affords the crude 14-fluoro-(Z)-3-tetradecen-1-yl-tetrahydropyranyl ether. Purification by flash chromatography gives 14-fluoro-(Z)-3-tetradecen-1-yl-tetrahydropyranyl ether 353.6 mg (97%) as a clear colorless oil: Rf=0.65 hexane/ethyl acetate (7:3, v/v); IR (film) $v3025$ (C=CH), 2850–2950 (alkane CH); and $^1$H-NMR (CDCl$_3$) $\delta$1.20–1.80 (m, 22H), 2.15 (m, 2H), 2.35 (br q, J=5 HZ, 2H), 3.60 (m, 4H), 4.41 (dt, J=48 Hz, 6 Hz, 2H), 4.65 (br s, 1H), 5.41 (m, 2H).

EXAMPLE 11

14-fluoro-(Z)-3-tetradecen-1-ol

Following the procedure described in Example 6 using 353.6 mg (1.26 mmol) of 14-fluoro-(Z)-3-tetradecen-1-yl tetrahydropyranyl ether and 350 mg Dowex in about 10 ml of methanol affords 14-fluoro-(Z)-3-tetradecen-1-ol. Purification by flash chromatography affords 14-fluoro-(Z)-3-tetradecen-1-ol (211.8 mg, 73%) as a clear colorless oil: Rf=0.27, hexane/ethyl acetate (7:3, v/v); IR (film) $v3200$–3500 (OH), 3025 (alkane CH); and $^1$H-NMR (CDCl$_3$) $\delta$1.20–1.70 (m, 16H), 2.10 (m, 2H), 2.39 (br q, J=5 Hz, 2H), 3.65 (t, J=6 Hz, 2H), 4.41 (dt, J=48 Hz, 6 Hz, 2H), 5.45 (m, 2H).

EXAMPLE 12

6-fluoro-1-bromo-hexane

Following the procedure detailed in Example 2 but using 2.0779 g (11.48 mmol) of 6-bromo-1-hexanol, and 1.455 mL (11.48 mmol) of DAST and purifying by evaporative distillation affords the 6-fluoro-1-bromohexane.

EXAMPLE 13

10-fluoro-3-decyn-1-yl tetrahydropyranyl ether

Repetition of the procedure described in Example 3 using 0.7992 g (5.06 mmol) of 3-butyn-1-yl tetrahydropyranyl ether, 3.6 mL (5.06 mmol) of 1.39M n-butyl lithium in hexane and 1.117 g (6.07 mmol, 1.2 eq) of 6-fluoro-1-bromo-hexane followed by purification by flash chromatography affords 10-fluoro-3-decyn-1-yl tetrahydropyranyl ether (570 mg, 44%) as a clear colorless oil: Rf=0.58 hexane/ethyl acetate (7:3, v/v); IR (film) $v2850$–2950 (alcane CH); and $^1$H-NMR (CDCl$_3$) $\delta$1.20–1.95 (m, 14H), 2.15 (m, 2H), 2.45 (m, 2H), 3.65 (m, 4H), 4.42 (dt, J=48 Hz, 6 Hz, 2H), 4.65 (br s, 1H).

EXAMPLE 14

10-fluoro-(Z)-3-decen-1-yl-tetrahydropyranyl ether

The hydrogenation procedure of Example 4 is substantially repeated using 568.3 mg of 10-fluoro-3-decyn-1-yl tetrahydropyranyl ether, 24 mg of 5% palladium on barium sulfate and about 2 drops quinoline in 10 mL methanol. The reaction is stopped when 49.7 mL (2.22 mmol) of hydrogen has been absorbed. Purification by flash chromatography gives 10-fluoro-(Z)-3-decen-1-yl-tetrahydropyranyl ether 562.9 mg (99%) as a clear colorless oil: Rf=0.68 hexane/ethyl acetate (7:3, v/v); IR (film) $v3025$ (C=CH), 2850–2950 (alkane CH); and H NMR $\delta$1.20–1.80 (m, 16H), 2.05 (m, 2H), 2.23 (br q, J=5 Hz, 2H), 3.57 (m, 4H), 4.40 (dt, J=48 Hz, 6 Hz, 2H), 4.55 (br s, 1H), 5.40 (m, 2H).

EXAMPLE 15

10-fluoro-(Z)-3-decen-1-ol

The procedure of example 6 is substantially repeated using 562.9 mg (2.20 mmol) of 10-fluoro-(Z)-3-decen-1-yl-tetrahydropyranyl ether and 500 mg Dowex in about 20 ml methanol. Purification of the resultant product by flash chromatography gives 10-fluoro-(Z)-3-decen-1-ol (344 mg, 90%) as a clear colorless liquid: Rf=0.39 hexane/ethyl acetate (7:3, v/v); IR (film) $v3100$–3600 (OH), 3000 (C=CH), 2850–2950 (alkane CH); and H NMR (CDCl$_3$) $\delta$1.20–1.65 (m, 8H), 2.05 (m, 2H), 2.77 (br q, J=5 Hz, 2H), 3.60 (t, J=6 Hz, 2H), 4.37 (dt, J=48 Hz, 6 Hz, 2H), 5.42 (m, 2H).

EXAMPLE 16

Methyl 6-hydroxy-(Z)-3-hexenoate

A solution of technical grade 1-methoxy-1,4-cyclohexadiene (2.0 g, 18.16 mM, 2.13 mL) in 20 mL of methanol is cooled to $-78°$ C. and treated with 1 eq. of ozonized oxygen gas with efficient stirring (Corey et al., J. Am. Chem. Soc. 90, 5618, 1968 and Pappas et al., Tetrahedron Letters, 4273, (1966)). While still at $-78°$ C., the solution is flushed with nitrogen, and dimethylsulfide (1.5 mL, 20 mmol) is added. The solution is stirred at $-10°$ C. for 1 hour, then at ice bath temperature for 1 hour, and finally at room temperature for 1 hour. Methanol and excess dimethyl sulfide are removed in vacuo and to the residue is added anhydrous ethanol (25 mL) followed by sodium borohydride (0.219 g, 6.8 mmol, 1.5 eq). The mixture is stirred for 1 hour at room temperature and the ethanol removed in vacuo. The residue is then diluted with ether (150 mL) and the ether layer washed with 10% hydrochloric acid (75 mL). The water layer is extracted with ether (4×50 mL) and the combined organics are washed with saturated sodium bicarbonate (25 mL) and dried over magnesium sulfate. Purification by flash chromatography, hexane/ethyl acetate (70:30, v/v) affords methyl 6-hydroxy-H-(Z)-3-hexenoate (1.24 g, 54%) as a clear yellowish liquid: Rf=$v$0.26, hexane/ethyl acetate (1:1, v/v); IR (film) 3200–3600 (OH), 2850–3000 (C=CH, Alkane CH), 1730 (C=O); and H NMR (CDCl$_3$) $\delta$2.30 (m, 2H), 3.15 (br d J=6 Hz, 2H), 3.62 (t, J=6 Hz, 2H), 3.66 (S, 3H), 5.62 (m, 2H). $^{13}$C NMR (CDCl$_3$) $\delta$ (rel intens.) 30.96 (108), 32.62 (118), 51.48 (76), 61.21 (125), 123.13 (103), 129.62 (109), 171.64 (26).

EXAMPLE 17

Methyl 6-tetrahydropyranyl-(Z)-3-hexenoate

A solution of methyl 6-hydroxy-(Z)-3-hexenoate (0.7684 g, 5.3 mmol), 3,4-dihydropyran (0.72 mL, 7.9 mmol, 1.5 eq) and pyridinium p-toluenesulfonate (PPTS, 125 mg, 0.5 mmol) in methylene chloride (25 mL) is stirred for 4 hours at room temperature. The solution is then diluted with ether (150 mL), and the ether layer is washed with half-saturated brine (50 mL) to remove the catalyst, and dried over magnesium sulfate. Purification by flash chromatography using hexane/ethyl acetate (90:10, v/v) affords methyl 6-tetrahydropyranyloxy-(Z)-3-hexenoate (1.19 g, 99%) as a clear colorless oil: Rf=0.38, hexane/ethyl acetate (7:3, v/v), IR (film) ν2850–3000 (C═CH, alkane CH), 1740 (C═O) and H NMR (CDCl₃) δ1.45–1.65 (m, 6H), 2.35 (m, 2H), 3.10 (d, J=6 Hz, 2H), 3.30–3.70 (m, 4H), 3.58 (sS, 3H), 4.55 (br s, 1H), 5.65 (br t, J=6 Hz, 2H).

EXAMPLE 18

6-tetrahydropyranyloxy-(Z)-3-hexen-1-ol

To a mixture of lithium aluminum hydride (0.336 g, 8.85 mmol 1.2 eq.) in tetrahydrofuran (100 mL) at 0° C. is added 6-O-tetrahydropyranylmethyl-(Z)-3-hexenoate (3.1302 g, 14.75 mmol) in THF (10 mL) dropwise. The mixture is refluxed for 0.5 hours, cooled to room temperature and quenched by successive dropwise addition of water (about 3 drops), saturated sodium bicarbonate (about 3 drops) and water (about 6 drops). The solvent is removed in vacuo and the residue is diluted with ether (about 150 mL) and the ether layer is washed successively with 5% hydrochloric acid (25 mL), saturated sodium bicarbonate (25 mL), brine (25 mL) and dried over magnesium sulfate. Purification by flash chromatography using hexane/ethyl acetate (75:25, v/v) gives 6-tetrahydropyranyloxy-(Z)-3-hexen-1-ol (2.1159, 78%) as a clear colorless liquid: Rf=0.26, hexane/ethyl acetate (7:3, v/v), IR (film) ν3200–3550 (OH), 2825–3000 (C═CH, alkane CH); and ¹H NMR (CDCl₃) δ1.40–1.70 (m, 6H), 2.30 (m, 4H), 3.55 (t, J=6 Hz, 2H), 3.40–3.80 (m, 4H), 4.51 (br s, 1H), 5.54 (m, 2H).

EXAMPLE 19

1-iodo-6-tetrahydropyranyloxy-(Z)-3-hexene

To a solution of 6-tetrahydropyranyl-oxy-(Z)-3-hexen-1-ol (1.8824 g, 10.2 mmol), in dry pyridine (about 15 mL) at 0.° C. is added p-toluenesulfonyl chloride (2.9310 g, 15.3 mmol, 1.5 eq) in one portion. The mixture is stirred at 0° C. for 1 hour and then stored in the refrigerator (5° C.) overnight. The reaction mixture is cooled to 0° C. and most of the pyridine is removed in vacuo and ether (200 mL) added. The ether layer is washed successively with 5% hydrochloric acid (25 mL), saturated sodium bicarbonate (25 mL), brine (25 mL) and dried over magnesium sulfate. After filtration and removal of the ether, the crude product is diluted with dry acetone (20 mL), and dry sodium iodide (12.22 g, 82 mmol, 10 eq) is added. The mixture is stirred at room temperature for 3 hours and the volatiles are removed in vacuo. The residue is diluted with hexane (about 200 mL) and this solution is then extracted with aqueous sodium thisulfate, followed by brine. The organic layer is dried over magnesium sulfate, and the volatiles removed in vacuo. Purification by flash chromatography affords 1-iodo-6-tetrahydropyranyl-oxy-(Z)-3-hexene (2.5 g, 83%) as a clear yellowish oil: Rf=0.76, hexane/ethyl acetate (1:1, v/v); IR (film) ν 2850–3050 (C═CH, alkane CH); and ¹H-NMR (CDCl₃) δ 1.45–1.70 (m, 6H), 2.35 (br q, 5=6 Hz, 2H), 2.71 (br t, J=6 Hz), 2H), 3.15 (t, 2H), 3.30–3.85 (m,4H), 4.57 (br s, 1H) 5.57 (m, 2H).

EXAMPLE 20

6-tetrahydropyranyl-oxy-(Z)-3-hexen-1-triphenylphosphonium iodide

To a solution of 1-iodo-6-O-tetrahydropyranyloxy-(Z)-3-hexen-1 (4.4446 g, 14.3 mmol) in toluene/acetonitrile (40 mL, 3/1) is added reagent grade triphenylphosphine (4.5030 g, 17.19 mmol, 1.2 eq.) in one portion. The solution is stirred for 48 hours at 60° C. The mixture is then cooled, and the solvents removed in vacuo to give an oily solid. This residue is washed with anhydrous ether until 6-tetrahydropyranyl-oxy-(Z)-3-hexen-1-iodide (7.4 g,80%) is obtained as a white crystalline solid: ¹H-NMR δ (CDCl₃) δ 1.45–1.70 (m, 6H), 2.10–2.75(m,4H), 3.20–3.80 (m,6H), 4.57(br s, 1H), 5.45–5.75 (M, 2H), 7.70–7.85 (m,15H).

EXAMPLE 21

6-hydroxyhexanal

To a solution of 6-hexanolactone (4.0 g, 35 mmol) in toluene (100 mL) at −78° C. was added diisobutyl aluminum hydroxide (Baren, *J. Org. Chem.*, 30, 3564, 1965) (52.5 mmol, 1.5 eq, 52.5 mL of 1M DIBAL —H in toluene). The mixture is stirred for 1 hour at −78° C. after which time the reaction is quenched by dropwise addition of aqueous acetone acid (2:1). The mixture is then diluted with chloroform (about 200 mL) and the organic layer is washed successively with water (30 mL), saturated sodium bicarbonate (30 mL), brine (30 mL) and then dried over magnesium sulfate. The organic layer is removed in vacuo to yield 6-hydroxyhexanal (3.12 g, 78%) as a clear colorless liquid: Rf=0.19 hexane/ethyl acetate (1:1,v/v); IR (film) ν 3175–3550 (OH) 2850–2950 (alkane CH), 1720 (C═O); and ¹H-NMR (CDCl₃) δ 1.50–1.68(m, 6H), 2.47 (dt, J=6 Hz, 2.5 Hz, 2H), 3.65 (t, J=6 Hz, 2H), 9.77 (t, J=2.5 Hz, 1H).

In accordance with the above procedure, but where, in place of 6-hexanolactone, there is used 4-butanolactone, 8-octanolacetone or 10-decanolactone, there is obtained the corresponding 4-hydroxybutanol, 8-hydroxyoctanal or 10-hydroxydecanal.

EXAMPLE 22

12-hydroxy-(Z),(Z)-3,6-dodecadien-1-yl tetrahydropyranyl ether

An aliquot of 6-tetrahydropyranyl-oxy-3-hexen-1-triphenylphosphonium iodide in acetonitrile is transferred to a preweighed round bottom flask and the acetonitrile removed in vacuo. Dry benzene (10 mL) is added, and the benzene is then removed in vacuo to leave 1.1184 g (1.96 mmol) of 6-tetrahydropyranyl-oxy-(Z)-3-hexen-1-triphenylphosphonium iodide as an, anhydroxy solid. The salt is dissolved in dry tetrahydrofuran (about 20 mL) and n-butyl lithium, (1.96 mmol, 1.45 mL of 1.35M n-butyl lithium in hexane) is added at 0° C. The bright orange solution is stirred for 30 minutes at 0° C. and then followed by the rapid addition of 6-hydroxyhexanal (227.4 mg, 1.96 mmol) dissolved in THF/HMPA (9 mL, 1:2, v/v). The mixture is then stirred for 2 hours at 0° C. and quenched by the dropwise addition of water. The tetrahydrofuran is removed in vacuo and the residue is takep up in hexane (200 mL) and the hexane layer is washed successively with water (2×50 mL), brine (30 mL) and dried over magnesium sulfate. Removal of the solvent provides a crude mixture of 12-hydroxy-(Z)-(Z)-3,6-dodecadien-1-yl tetrahydropyranyl ether containing less than 5% (GLC) of the isomeric 12-hydroxy-(Z),(E)-3,6-dodecadien-1-yl tetrahydropyranyl ether. Purification by flash chromatography using hexane/ethyl acetate (80:20, v/v) affords 12-hydroxy-(Z),(Z)-3,6-dodecadien-1-yl tetrahydropyranyl ether (253 mg, 46%) as a clear slightly yellow oil: Rf=0.42 hexane/ethyl acetate (1:L v/v); IR (film) ν 3250–3550 (OH), 2850–3050 (C═CH, alkane CH); and ¹H-NMR (CDCl₃), δ 1.30–1.80 (m, 12H), 1.15 (br d, J=6 Hz, 2H), 2.35 (br q, J=6 Hz, 2H), 2.78 (br t, J=6 Hz, 2H), 3.30–3.85 (m, 4H), 3.65 (t, J=6 Hz, 2H), 4.56 (br s, 1H), 5.40 (br q, J=6 Hz, 4H).

In accordance with the above procedure, but wherein place of 6-hydroxyhexanal, there is utilized 4-hydroxybutanal, 8 hydroxyoctanal or 10-hydroxydecanal, there are obtained the corresponding 10-hydroxy-(Z),(Z),-3,6-decadien-1-yl, 14-hydroxy-(Z),(Z)-3,6-tetradecadien-1-yl, and 16-hydroxy-(Z),(Z)-3,6-hexadecadien-1-yl tetrahydropyranyl ethers and the corresponding (Z),(E) isomer of each. It is not necessary to remove the less active (Z,E), isomeric contaminants.

EXAMPLE 23

12-fluoro-(Z),(Z)-3,6-dodecadien-1-yl tetrahydropyranyl ether

A solution of dimethylaminotrimethylsilane (166.1 mg, 1.42 mmol, 1.41.eq) in trichlorofluoro methane (6 mL) is cooled to $-78°$ C. and diethylaminosulfurtrifluoride (DAST, 0.215 mL, 1.71 mmol, 1.91 eq) is added. The solution is stirred for 10 minutes at $-78°$ C. and 12-hydroxy-(Z),(Z)-3,6-dodecadien-1-yl tetrahydropyranyl ether (253.0 mg, 0.897 mmol, 1 eq.) in trichlorofluoromethane (1 mL) is added dropwise. The solution is stirred for 45 minutes at $-78°$ C., allowed to warm to room temperature and then stirred an additional 1 hour. A few crystals of sodium carbonate are added followed by the addition of ether (about 200 mL), and the ether layer is washed successively with saturated sodium bicarbonate (30 mL) and brine (25 mL) and then dried over magnesium sulfate. Purification by flash chromatography affords 12-fluoro-(Z),(Z)-3,6-dodecadien-1-yl tetrahydropyranyl ether (151.7 mg, 59.2%) as a clear yellowish oil: Rf=0.75, hexane/ethyl acetate (1:1,v/v); IR (film) $\nu$ 2850–3050 (C=CH, alkane); and H NMR (CDCl$_3$) $\delta$1.20–1.70 (m, 2H), 2.05 (m, 2H), 2.35 (br q, J=6 Hz, 2H), 2.75 (br t, J=6 Hz, 2H), 3.30–3.75 (m, 4H), 4.38 (dt, J=48 Hz, 6 Hz, 2H), 4.55 (br s, 1H), 5.37 (br q, J=6 Hz, 4H).

EXAMPLE 24

12-fluoro-(Z),(Z)-3,6-dodecadien-1-ol

A solution of 12-fluoro-(Z,Z)-3,6-dodecadien-1-yl tetrahydropyranyl ether (218.2 mg, 0.768 mmol) in methanol (10 mL) is treated with pyridinium-p-toluenesulfonate (Baren, *J. Org. Chem.*, 30, 3564, 1965) (PPTS, 20.6 mg, 0.08 mm) for 3 hours at 55° C. The solvent is evaporated and the residue is then diluted with ether (about 200 mL). The resultant ether layer is washed with half-saturated brine (50 mL) and dried (MgSO$_4$). Purification by flash chromatography using hexane/ethyl acetate (90:10, v/v) gives 126.3 mg (80%) of 12-fluoro-(Z),(Z)-3,6-dodecadien-1-ol as a clear colorless liquid: Rf=0.56 hexane/ethyl acetate (1:1, v/v); IR (film) $\nu$ 3150–3500 (OH), 2825–2910 (C=CH, alkane-CH); $^1$H NMR (CDCl$_3$) $\delta$ 1.35–1.55 (m, 6H), 2.10 (m, 2H), 2.35 (br q, J=6 Hz, 2H), 2.80 (br t, J=6 Hz, 2H), 3.64 (t J=6 Hz, 2H), 4.41 (dt, J=48 Hz, 6 Hz, 2H), 5.41 (m, 4H); and $^{13}$C NMR (CDCl$_3$) $\delta$ 24.71 (56), 24.98(58), 25.78(97), 27.12(95), 29.21(93), 29.84(52), 30.83(125), 62.22 (92), 84.14 (d, J=164 Hz, 51,41) 125.54 (93), 127.87 (91), 130.16 (96), 131.25(85).

EXAMPLE 25

In accordance with the procedures of Examples 23 and 24 immediately preceding but where in place of 12-hydroxy-(Z),(Z)-3,6-dodecadien-1-yl tetrahydropyranyl ether, there are utilized 12-hydroxy-(Z),(E)-3,6-dodecadien-1-yl,
10-hydroxy-(Z),(E)-3,6-decadien-1-yl
10-hydroxy-(Z),(Z)-3-decadien-1-yl,
14-hydroxy-(Z),(E)-3,6-tetradecadien-1-yl
14-hydroxy-(Z),(Z)-3,6-tetradecadien-1-yl
16-hydroxy-(Z),(E)-3,6-hexadecadien-1-yl
16-hydroxy-(Z),(Z)-3,6-hexadecadien-1-yl tetrahydropyranyl ethers there are obtained the corresponding
12-fluoro-(Z),(E)-3,6-dodecadien-1-ol
10-Fluoro(Z),(E)-3,6-decadien-1-ol
10-fluoro-(Z),(Z)-3,6-decadien-1-ol
14-fluoro-(Z),(E)-3,6-tetradecadien-1-ol
14-fluoro-(Z),(Z)-3,6-tetracadien-1-ol
16-fluoro-(Z),(E)-3,6-hexadecadien-1-ol and
16-fluoro-(Z),(Z)-3,6-hexadecadien-1-ol

PREPARATION OF BAIT BLOCKS 16-fluoro-9-(E)-hexadecen-1-ol is dissolved in acetone as a 0.1, 0.05, 0.01 percent solution.

Over dried wood blocks are vacuum impregnated in the solution in accordance with the method of Maudlin and Rich (J. Econ. Entomol 73 123 (1980)).

The wood blocks are heated to 50° C. for 24 hours and fixed to the bottom of a container. The container is depressurized down to 110 mm Hg for 20 minutes and the blocks allowed to cool. While still under vaccuum, the container is flooded with fluoroalkanol/acetone solution to sufficient depth to submerge the blocks. The vacuum is then released and the blocks permitted to soak for 30 minutes. The blocks are then removed from the solution and permitted to dry under ambient conditions.

The blocks are utilized by burying them under the soil in areas proximate to termite nests.

If desired the blocks may be partially encased in plastic do discourage the attention of larger animals.

Other cellulosic substrates, such as paper, pressboard, cardboard, leaf litter or dry grass may be used as bait materials for coating for impregnation. This allows for the targeting of the toxicant to a variety of arboreal subterranean and mound-building tropical termites as well as the eastern subterranean termite *Reticulitermes flavipes* as mentioned above.

In accordance with the above procedure wood blocks may be similarly impregnated with:
14-fluoro-3-(Z)-tetradecen-1-ol
12-fluoro-3-(Z)-dodecen-1-ol
12-fluoro-3,6-(Z),(Z)-dodecadien-1-ol
12-fluorododecan-1-ol
10-fluoro-3-(Z)-decen-1-ol or any of the w-fluoro alken-1-ols or w-fluoroalkadien-1-ols prepared in accordance with the present invention, to obtain a similar product.

What is claimed is:

1. An alpha-fluoro-omega-hydroxy straight chain alkene having a chain length of from 10 to 16 carbon atoms and having from 1 to 4 double bonds therein.

2. A compound according to claim 1 having one or two double bonds.

3. A compound according to claim 1 containing 12 or 14 carbon atoms.

4. A compound according to claim 3 containing one or two double bonds.

5. A compound according to claim 4 wherein the double bonds are cis double bonds.

6. A compound according to claim 4 wherein the compound contains 12 carbon atoms.

7. A compound according to claim 6 wherein the double bonds are cis double bonds.

8. A compound according to claim 7 which is 12-fluoro-(Z)-3-dodecen-1-ol.

9. A compound according to claim 7 which is 12-fluoro-(Z),(Z)-3,6-dodecadien-1-ol.

10. A compound according to claim 5 which is 14-fluoro-(Z)-3-tetradecen-1-ol.

11. A compound according to claim 2 which is 10-fluoro-(Z)-3-decen-1-ol.

12. A compound according to claim 2 of the formula:

$$F-(CH_2)_{n-4}-CH=CH-(CH_2)_2OH$$

wherein n is from 10 to 16.

13. A compound according to claim 2 of the formula:

$$F-(CH_2)_{n-7}-CH=CH-CH_2-CH=CH-(CH_2)_2OH$$

wherein n is from 10 to 16.

14. An termiticidal composition comprising a water insoluble solid carrier ingestible by termites, having absorbed thereon a termiticidally effective amount of an alpha-fluoro-omega-hydroxy straight chain hydrocarbon having a chain length of from 10 to 16 carbon atoms and having from 0 to 4 double bonds therein.

15. A composition of claim 14 additionally comprising a termite attractant composition.

16. A composition of claim 14 or 15 wherein the termiticidally composition is 12-fluorododecanol.

17. A composition according to claim 14 wherein the alpha-fluoro-omega-hydroxy straight chain hydrocarbon is an alpha-fluoro-omega-hydroxy straight chain alkene having a chain length of from 10 to 16 carbon atoms and having from 1 to 4 double bonds therein.

18. A composition according to claim 17 wherein the alkene has one or two double bonds.

19. A composition according to claim 18 wherein the alkene contains 12 or 14 carbon atoms.

20. A composition according to claim 19 wherein the double bonds are cis double bonds.

21. A composition according to claim 19 wherein the alkene contains 12 carbon atoms.

22. A composition according to claim 21 wherein the double bonds are cis double bonds.

23. A composition according to claim 21 wherein the alpha-fluoro-omega-hydroxy straight chain hydrocarbon is 12-fluoro-(Z)-3-dodecen-1-ol.

24. A composition according to claim 21 wherein the alpha-fluoro-omega-hydroxy straigh chain hydrocarbon is 12-fluoro-(Z),(Z)-3,6-dodecadien-1-ol.

25. A composition according to claim 17 wherein the alpha-fluoro-omega-hydroxy straight chain hydrocarbon is 14-fluoro-(Z)-3-tetradecen-1-ol.

26. A composition according to claim 17 wherein the alpha-fluoro-omega-hydroxy straight chain hydrocarbon is 10-fluoro-(Z)-3-decen-1-ol.

27. A composition according to claim 17 wherein the alpha-fluoro-omega-hydroxy straight chain hydrocarbon is of the formula:

$$F-(CH_2)_{n-4}-CH=CH-(CH_2)_2OH$$

wherein n is from 10 to 16.

28. A composition according to claim 17 wherein the alpha-fluoro-omega-hydroxy straight chain hydrocarbon is of the formula:

$$F-(CH_2)_{n-7}-CH=CH-CH_2-CH=CH-(CH_2)_2OH$$

wherein n is from 10 to 16.

29. A composition according to claim 14 wherein the water-insoluble solid carrier is a cellulosic substrate.

30. A method of combatting termites which comprises providing an attractant termiticidal composition according to claim 14 to a location proximate to termite nests.

31. A method of combatting termites which comprises providing an attractant termiticidal composition according to claim 15 to a location proximate to termite nests.

32. A method of claim 31 wherein the termiticidal composition is 12-fluorododecanol.

33. A method of combatting termites which comprises providing an attractant termiticidal composition according to claim 17 to a location proximate to termite nests.

34. A method of combatting termites which comprises providing an attractant termiticidal composition according to claim 23 to a location proximate to termite nests.

35. A method of combatting termites which comprises providing an attractant termticidal composition according to claim 24 to a location proximate to termite nests.

36. A method of combatting termites which comprises providing an attractant termiticidal composition according to claim 23 wherein the water-insoluble solid carrier is a cellulosic substrate.

37. A method of combatting termites which comprises providing an attractant termiticidal composition according to claim 24 wherein the water-insoluble solid carrier is a cellulosic substrate.

38. A method of combatting termites which comprises providing an attractant termiticidal composition according to claim 27 wherein the water-insoluble solid carrier is a cellulosic substrate.

39. A method of combatting termites which comprises providing an attractant termiticidal composition according to claim 28 wherein the water-insoluble solid carrier is a cellulosic substrate.

* * * * *